United States Patent
Astl et al.

(10) Patent No.: US 12,064,230 B2
(45) Date of Patent: Aug. 20, 2024

(54) METHOD, DEVICE, AND SYSTEM FOR ASCERTAINING AT LEAST ONE STATE VARIABLE OF A LIVESTOCK ORGANISM

(71) Applicant: Smaxtec Animal Care GmbH, Graz (AT)

(72) Inventors: Michael Astl, Graz (AT); Philipp Kulich, Graz (AT); Stefan Brandstätter, Graz (AT); Manuel Frech, Hinterstoder (AT); Matthias Wutte, Graz (AT); Stefan Rosenkranz, Graz (AT)

(73) Assignee: smaXtec animal care GmbH, Graz (AT)

( * ) Notice: Subject to any disclaimer, the term of this patent is extended or adjusted under 35 U.S.C. 154(b) by 298 days.

(21) Appl. No.: 17/292,949

(22) PCT Filed: Nov. 13, 2019

(86) PCT No.: PCT/AT2019/060386
§ 371 (c)(1),
(2) Date: May 11, 2021

(87) PCT Pub. No.: WO2020/097655
PCT Pub. Date: May 22, 2020

(65) Prior Publication Data
US 2022/0000388 A1    Jan. 6, 2022

(30) Foreign Application Priority Data

Nov. 13, 2018  (AT) ............... A 50986/2018

(51) Int. Cl.
| | | |
|---|---|---|
| *A61B 5/07* | (2006.01) | |
| *A01K 29/00* | (2006.01) | |
| *A61B 5/11* | (2006.01) | |
| *G01P 15/18* | (2013.01) | |

(52) U.S. Cl.
CPC ............ *A61B 5/073* (2013.01); *A01K 29/005* (2013.01); *A61B 5/1118* (2013.01); *G01P 15/18* (2013.01); *A61B 2503/10* (2013.01); *A61B 2562/0219* (2013.01)

(58) Field of Classification Search
CPC .... A01K 11/007; A01K 29/00; A01K 29/005; A61B 5/07; A61B 5/073; A61B 5/1118; A61B 2503/10; A61B 2562/0219; G01P 15/08; G01P 15/18
See application file for complete search history.

(56) References Cited

U.S. PATENT DOCUMENTS

| 8,823,515 B2 | 9/2014 | Rettedal et al. |
| 9,844,206 B2 | 12/2017 | Rettedal et al. |
| 10,098,328 B2 | 10/2018 | van Dijk et al. |
| 2003/0176815 A1* | 9/2003 | Baba ................. A61B 5/02438 600/595 |
| 2009/0187392 A1 | 7/2009 | Riskey et al. |
| 2009/0318783 A1* | 12/2009 | Rohde ................. A61B 5/6861 600/302 |
| 2010/0119133 A1* | 5/2010 | Glukhovsky .......... A61B 1/041 382/128 |
| 2018/0271066 A1* | 9/2018 | Balbian ................ A01K 11/007 |
| 2018/0310885 A1 | 11/2018 | Kim |
| 2018/0368362 A1* | 12/2018 | Breitenstein ............. A61B 5/01 |

FOREIGN PATENT DOCUMENTS

| DE | 19901124 | 7/2000 |
| WO | WO2017/103239 | 6/2017 |

OTHER PUBLICATIONS

EP application No. 19 805 118.7. EPO Communication dated Jun. 8, 2022. 3 pages. With English Translation.
PCT/AT2019/060386. Written Opinion (English translation). Mailed Jan. 15, 2020.

* cited by examiner

*Primary Examiner* — May A Abouelela
*Assistant Examiner* — Anna Roberts
(74) *Attorney, Agent, or Firm* — Joseph E. Maenner; Maenner & Associates, LLC

(57) ABSTRACT

The invention relates to a method for determining at least one state variable of the organism of at least one farm animal, wherein at least one probe device for measurement of at least one physical parameter is disposed in the gastro-intestinal tract of the farm animal and at least one evaluation unit is disposed outside the gastro-intestinal tract of the farm animal. The method performs the following steps: determining at least one first physical parameter by the probe device; converting the first physical parameter into a first state variable of the organism of the farm animal in a probe control unit of the probe device; transmitting the first state variable by the probe device to the evaluation unit; and converting the first state variable into a second state variable in the evaluation unit.

11 Claims, 4 Drawing Sheets

METHOD, DEVICE, AND SYSTEM FOR ASCERTAINING AT LEAST ONE STATE VARIABLE OF A LIVESTOCK ORGANISM

BACKGROUND OF THE INVENTION

The invention relates to a method for determining at least one state variable of the organism of at least one farm animal, wherein at least one probe device for measuring at least one physical parameter is disposed in the gastro-intestinal tract of the farm animal and at least one evaluation unit is disposed outside the gastro-intestinal tract of the farm animal. The invention additionally relates to a probe device for measuring at least one state variable of the organism of a farm animal, wherein the probe device can be arranged in the gastro-intestinal tract of the farm animal. Furthermore, the invention relates to a system comprising at least one evaluation unit and at least one such probe device.

Agriculture is increasingly developing throughout the world in the direction of large farms. In this context, for example, for farmers herd management is becoming increasingly difficult in the keeping of farm animals, particularly with regard to monitoring the health of individual animals or to allocating feeds based on performance. The parameters which are important for the well-being and the feed requirement of the individual animals comprise, in addition to external state information such as, for example, temperature, oxygen content or air humidity in the aft in the shed, also physiological parameters such as, for example, pH of the gastric juice, body temperature or others.

With increasingly large farms, customized feeding is hardly possible as a result of these numerous parameters; also systems of disease in individual animals frequently cannot be identified in good time. In order to nevertheless enable species-appropriate husbandry and economical production, it is of enormous importance for the farmer to be informed about the parameters which are important for the well-being of the animals.

For this purpose, electronic management aids are increasingly being used DE 199 01 124 A1, for example, describes a probe in bolus form which can measure sensors for measuring various physiological state variables such as pressure, temperature, conductivity, pH or ammonia content and is inserted in the gastro-intestinal tract of cattle. AT 509 255 B1 of the applicant describes a similar probe unit in which the measurement data can be transmitted in a wireless manner, wherein the measurement sensor system is at least partially surrounded by a cylindrical protection device inside an acid-resistant casing for protection from mechanical damage. The probe unit can radio data to base stations distributed in a shed and can be operated or read out via this by a control device.

In the case of such devices, it needs to be taken into account in particular that a long-term function according to the lifetime or usage duration of the farm animal is required and at the same time, the read-out of data through the arrangement inside the farm animal requires a certain transmission power.

Thus, the focus is increasingly on purely physical measurement methods which promise an extension of the run times of these devices.

For example, WO 2017/103239 A1 describes a device in which in particular gastric pressure, temperature and motility of a farm animal are recorded. For this purpose a pressure sensor is used which, by means of a gastight region with elastically deformable wall, can measure the movements of the stomach, i.e. the gastric motility and can obtain measured values over at least 60 days.

Furthermore, the use of temperature and movement sensors to determine the total movement of the animal is described wherein the determined data can be sent to a receiver via a telemetric device.

A disadvantage of this is in particular that data recording and transmission take place with major expenditure of energy and usage is only possible over a limited time interval.

DE 299 11 803 U1 describes a device which can be inserted in the stomach of a farm animal to determine the gastric motility, i.e. the strength and frequency of gastric movements. For this purpose a piezoelectric sensor is provided which records the pressure changes in the stomach of the farm animal and which data is read out after recovery via a computer interface or is transmitted to a receiving station during operation. In contrast to acceleration sensor, the "motility or its effect on the feed in the stomach" should be measured directly. Disadvantages here are in particular the time-limited usability and the inaccuracy of the measurement which is obtained due to the technology used.

WO 2016/036303 A1 proposes a solution in which an acceleration sensor is fastened to the neck of a farm animal in order to measure chewing movements of the jaw during rumination and thus determine rumination times. Since the sensor is not disposed inside the farm animal, a good data transmission can be ensured, in addition, an energy supply unit can be changed without any complications. However a particular disadvantage is that due to the external arrangement on the neck, movement signals are also measured which do not allow any direct prediction of the health of the farm animal. Furthermore, damage can result if the farm animal with the acceleration sensor knocks against obstacles or other animals or attempts to pull this off.

BRIEF SUMMARY OF THE INVENTION

It is therefore the object of the invention to eliminate the aforesaid disadvantages and provide a method or a probe device and a system containing this by means of which health-relevant state variables of farm animals can be recorded in a simple and reliable manner over a long time interval.

This object is achieved by the initially mentioned method according to the invention by the following steps:
  a) determining at least one first physical parameter by the probe device;
  b) converting the first physical parameter into a first state variable of the organism of the farm animal in a probe control unit of the probe device;
  c) transmitting the first state variable by the probe device to the evaluation unit;
  d) converting the first state variable into a second state variable in the evaluation unit.

By dividing the steps of generating information relating to the farm animal from physical parameters between the probe device and the evaluation unit, an energy-saving, transmission-friendly procedure is possible which enables a rapid operation with a long usage duration.

Advantageously the first state variable comprises a state variable which in step c) can be transmitted with a lower data transmission rate than the first physical parameter and/or the second state variable. As a result, the required bandwidth and transmission time is reduced due to the conversion, which results in a reduced power consumption on the side of the probe device and the lowest possible loading of the transmission medium, which is an important factor in particular in real usage of numerous probe device in agricultural businesses. In one variant of the invention, the first state variable can be subjected to a compression process before transmission in step c) in order to further reduce the data rate to be transmitted and thus increase the advantages with regard to power consumption and bandwidth.

Favourably, the first physical parameter can be converted into the first state variable with lower computational expenditure than the first physical parameter into the second state variable and/or the first state variable into the second state variable. As a result, resource- and therefore energy-consuming processes can be shifted to the evaluation unit whilst the probe device is protected in this respect.

In variants of the invention, the determination of the first physical parameter in step a) takes place in at least one of the following manners; continuously; at regular intervals; continuously as soon as a physical parameter measured by the probe device, in particular the first physical parameter, has exceeded a threshold value; at regular intervals, as soon as a physical parameter measured by the probe device, in particular the first physical parameter, has exceeded a threshold value; continuously or at regular intervals for a predefined time interval as soon as a physical parameter measured by the probe device, in particular the first physical parameter, exceeds a threshold value. Optionally the threshold value is either stored predefined on the probe device or is transmitted from the evaluation unit in an occasion-related manner to the probe device or consists of a base threshold value and an adaptable dynamic value added to the base threshold value or subtracted from the base threshold value depending on the behaviour of the first physical parameter. As a result, energy of the probe device can be additionally saved.

Favourably, the first physical parameter in step a) comprises the acceleration, in particular the acceleration in all three spatial directions of a Cartesian coordinate system.

The first state variable in step b) comprises the motility, in particular the duration and/or the periodicity and/or the frequency of the motility. A variety of information about the state of a farm animal can be obtained from the motility.

In order to place the measured values in an overall context or in order to enable time precision, in step b) the first state variable is verified with a real-time signal of a clock generator provided in the probe device and/or a temperature signal of a temperature sensor provided in the probe device.

A high practical benefit of the method is obtained if the second state variable in step d) comprises one of the following state variables of the organism of the farm animal: rumination, heart beat, feeding time (can include both the beginning and/or end and also the duration of feeding). In other words, quantities relating in particular to the state and progress of the digestive tract/process can be used as second state variables, for example, the rumination or ruminating activity by means of the duration of the contractions of the motility and/or its periodicity and/or frequency.

In one variant of the method step a) is divided into the following substeps:
  a1) determining the acceleration of the probe device in one or more spatial directions of a Cartesian coordinate system;
  a2) determining the first physical parameter by carrying out at least one of the following steps: summing absolute values of the acceleration values determined in step a1, summing the squares of the acceleration values determined in step a1, root of the sum of the squares of the acceleration values determined in step a), arctan of the acceleration values determined in step a) for the y axis and z axis of the Cartesian coordinate system, arctan of the root of the sum of the squares of the acceleration values determined in step a1) and the x axis of the Cartesian coordinate system.

In a further variant, in step c) the first state variable is transmitted as a binary rectangular signal to the evaluation unit. Favourably in step b) in order to determine the first state variable, measured values of the first physical parameter which are greater than, in particular greater than or equal to a threshold value, are assigned the value "1" and measured values of the first physical parameter which are lower than a threshold value are assigned the value "0". As a result, the amount of data to be transmitted can be drastically reduced.

Favourably directly before step c) in a probe control unit of the probe device and/or before carrying out step d) in the evaluation unit a validation step is carried out in order to check the plausibility of the values of the first state variable of the organism of the farm animal. In other words, either in the probe control unit of the probe device, in the evaluation unit or in both it is checked by means of a validation step whether the values of the first state variable of the organism are plausible. Plausible means here that the values lie within the permissible or predicted ranges or the ranges occurring in the application such as in particular are stored in the probe control unit or the evaluation unit or both. For plausible values the execution of step c) is carried out, i.e. the transmission to the evaluation unit and/or on the evaluation unit the conversion into the second state variable. Non-plausible values are not used for the further process, i.e. are not transmitted or replaced by an error code to the evaluation unit and/or not used for the evaluation in the evaluation unit. It can thus be prevented that incorrect measurements which can, for example, be caused by harsh environmental conditions can disadvantageously influence the accuracy of the results.

The object of the invention is further achieved by an initially mentioned probe device according to the invention whereby the probe device can be arranged in the gastro-intestinal tract of the farm animal and comprise at least the following components arranged in a housing:
  at least one sensor element for measuring at least one physical parameter in the gastro-intestinal tract of the farm animal,
  at least one transmitting device, preferably with at least one antenna for the wireless transmission and receipt of information and
  at least one probe control unit which is adapted for carrying out steps a) to c) of an aforesaid method.

Favourably at least one of the following sensor elements is provided in the probe device: acceleration sensor, acceleration sensor for measuring the acceleration in all three spatial directions of a Cartesian coordinate system, temperature sensor, pH sensor, clock generator, real-time clock, camera element. Other types of sensor can also be used.

More possibilities for using the probe device according to the invention are obtained if at least one storage element connected to the probe control unit is provided, in particular at least one RAM and/or at least one ROM storage element. As a result, physical parameters or state variables can be stored if no direct transmission to an evaluation unit is possible or desired.

The object of the invention is additionally achieved by an initially mentioned system comprising at least one evaluation unit and at least one probe device described above wherein the above-described method can be carried out with the system. As a result, a comprehensive monitoring of larger herds of farm animals is possible.

BRIEF DESCRIPTION OF THE DRAWINGS

The invention is explained in detail hereinafter with reference to a non-restrictive exemplary embodiment which is shown in the drawings. The drawings only serve for illustration purposes and thus do not restrict the invention in any way. In the figures.

DETAILED DESCRIPTION OF THE INVENTION

For reasons of clarity the same elements in the different figures are provided with the same reference numbers.

Figure 1:
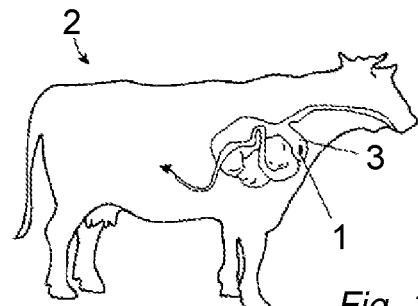
FIG. 1 shows a cow as an exemplary farm animal and the arrangement of a probe unit in its gastro-intestinal tract.

FIG. 1 shows a cutaway view of a cow 2, wherein the cow 2 here is only mentioned as a possible example for a farm animal, in particular a ruminant farm animal, in the gastro-intestinal tract 3 of which a probe device 1 according to the exemplary embodiment of the invention can be introduced. Other suitable ruminant farm animals would be, for example, sheep, goats or also wild ruminants such as red deer.

The feed ingested and chewed by the cow 2 enters into its gastro-intestinal tract 3, for example into the rumen or the reticulum ("Reticulum"). From the reticulum the ingested feed is on the one hand transported further into the rumen, on the other hand is transported back into the mouth of the cow 2 for ruminating. Any effects or conclusions on the state of health of the animal can be determined from measurement of the state variables of the organism of the cow 2 or the content of the gastro-intestinal tract 3. If the pH is too low, this can result in a dangerous ruminal acidosis, changes in the heart beat rate, rumen motility, ruminating and movement activity, for example, allow conclusions to be drawn on the presence of milk fever. The probe device 1 is thus arranged in the gastro-intestinal tract 3 of the animal in order to make it possible to determine state variables of the organism of the farm animal by means of the determination of physical parameters. In particular, good results can be achieved if the probe device 1 is located permanently in an end position in the reticulum.

Figure 2:
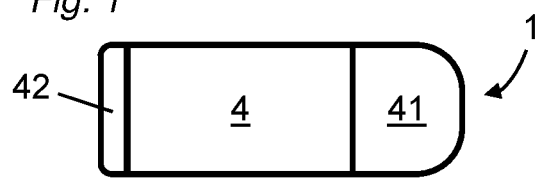
FIG. 2 shows a side view of a probe device according to the invention in the closed state.
Figure 3:
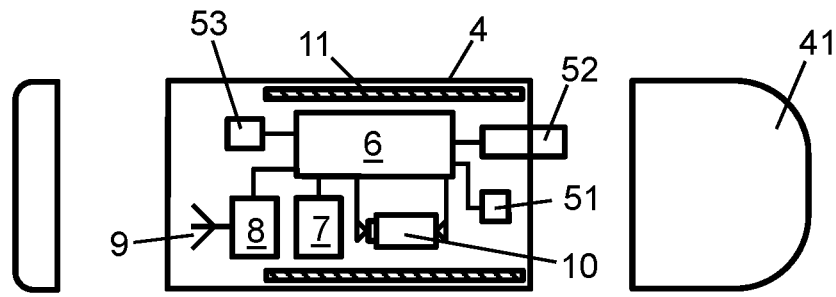
FIG. 3 shows a schematic view of a probe device according to the invention and its components.

FIG. 2 shows schematically a side view of the probe device 1 whereas FIG. 3 shows a schematic partially transparent view of an exemplary embodiment of the probe device 1: a first sensor element 51 and a second sensor element 52 are arranged inside a housing 4 with a first closure element 41 and a second closure element 42. The first sensor element 51 can be an acceleration sensor, the second sensor element 52 is implemented as a temperature sensor. In addition or instead, other sensors can also be used, e.g. those for measurement of temperature, pH, density, pressure, conductivity, sound, optical properties or of oxygen, $CO_2$, ammonia, glucose, volatile fatty acids, acetate, propionate, butyrate and lactate. Furthermore, a clock generator 53, e.g. an RTC ("Real Time Clock") is disposed in the probe device 1. The clock generator 53 can be implemented as an RTC as described and output an absolute time value. In one variant the clock generator 53 can also output a relative time value, e.g. the time which has passed or the clock rate since activation of the sensor device 1. The determination of an absolute time value can then be made downstream, e.g. on an evaluation unit 12 (see FIG. 4 and relevant description further below).

The sensor elements 51, 52 and the clock generator 53 are connected to a probe control unit 6 which is used to control the probe device 1. The probe control unit 6 is implemented for example as a suitably programmed microprocessor. The probe control unit 6 monitors and processes the data from the sensor elements 51, 52. A storage element 7, for example a memory chip or an SD card, can be provided for storing the data. The storage element 7 stores both measured values of the sensor elements 51, 52 and also operating parameters of the probe device 1 such as radio frequency (for communication with an evaluation unit 12), transmission channel, system time but also configuration parameters such as, for example, the scanning rate of the acceleration sensor, scanning rate of the conversion into the first state variable and others.

Figure 4:
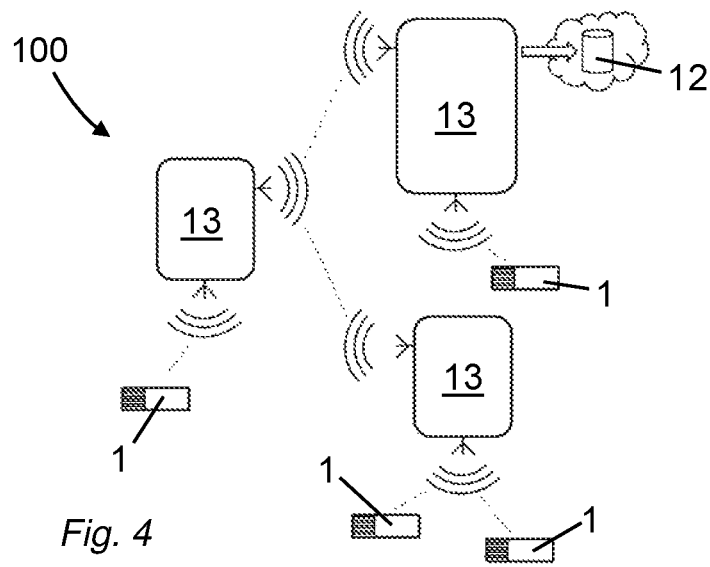
FIG. 4 shows a schematic diagram of a system according to the invention with a plurality of probe devices and an evaluation unit.

Data are transmitted via a transmitting device 8 which has an antenna 9, for example an evaluation unit 12 which is disposed in the surroundings of the farm animal 2 (see FIG. 4). Favourably the transmitting device 8 is designed as a transmitting-receiving device which can both transmit and also receive data.

The energy supply to the probe device 1 is accomplished, for example, via an energy supply device 10, which, for example, can be implemented as a battery, rechargeable battery or capacitor (advantageously a thin-film or supercapacitor). A recharging by "energy harvesting" or other methods is also possible.

In the depicted exemplary embodiment the described components according to the initially mentioned AT 509 255 B1 are enclosed inside the casing 4 by a hollow protective device 11 surrounding at least the energy supply device 10 which protects against mechanical action. This therefore prevents the farm animal from biting through the probe device 1 and in particular the components located therein, especially the energy supply device 10 if it is regurgitated into the mouth in the course of ruminating. The protective device 11 can in this case be fabricated from any resistant material, for example, from plastics or metals.

FIG. 4 shows an exemplary embodiment of a system 100 with a plurality of described probe devices 1—for reasons of clarity the farm animals in whose gastro-intestinal tract the probe devices 1 are arranged are not shown—and an evaluation unit 12 by means of which the probe devices 1 communicate in a wireless manner. In order to increase the range or in order to reduce the necessary transmission power, in the depicted exemplary embodiment a plurality of transmitting/receiving units 13 are provided between evaluation unit 12 and the transmitting devices 1, which function as relays but need not necessarily be present. As a result, a star-shaped architecture for application of the LoRa™ network protocol (or "LoRaWAN"-"Long Range Wide Area Network") can be implemented, wherein the probe devices 1 form the terminals and the transmitting/receiving units 13 as gateways send the data packets to the evaluation unit 12, e.g. a network server. The evaluation unit 12 can therefore, for example, be a mobile or stationary computer on which the corresponding evaluation routines run or can consist of a connection to a corresponding server via the internet.

In the described probe devices 1 particular attention is paid to ensuring the longest possible continuous operation. This can be achieved on the one hand by using powerful energy supply devices 10, on the other hand by particularly economical operation. This can advantageously be achieved whereby as far as possible only processes which are not very computing-intensive run in the probe device 1 or its probe control unit 6 but the complex calculations are shifted into the evaluation unit 12 which is located outside the gastro-intestinal tract 3 of the farm animal and therefore can be operated more easily, e.g. using the power network. In addition, care is taken to ensure that the amount of data which is transmitted from the probe device 1 to the evaluation unit 12 should be kept as small as possible with maximum information content.

In the described method therefore in a step a) a first physical parameter is determined by the probe device 1 or its sensor devices 51, 52. In this case, physical parameters are understood as parameters which characterize the physical conditions in the gastro-intestinal tract 3 of the farm animal, e.g. temperature, pH, acceleration values, image information and the like. In the present exemplary embodiment the acceleration, in particular the acceleration in all three spatial directions of a Cartesian coordinate system in which the probe device 1 is located is used which is determined using the first sensor element 51, the acceleration sensor.

For particularly energy-saving determination of the first physical parameter, this is accomplished in at least one of the following manners: continuously, the probe device 1 is therefore always activated;
at regular intervals, the probe device 1 is therefore activated at certain time points for the measurement but in the meantime remains deactivated or at least partially in an energy-saving state;
continuously as soon as a physical parameter measured by the probe device 1, in particular the first physical parameter, has exceeded a threshold value;
at regular intervals, as soon as a physical parameter measured by the probe device 1, in particular the first physical parameter, has exceeded a threshold value;
continuously or at regular intervals for a predefined time interval as soon as a physical parameter measured by the probe device 1, in particular the first physical parameter, exceeds a threshold value.

The said threshold value is either stored predefined on the probe device 1 or is transmitted from the evaluation unit 12 to the probe device 1 in an occasion-related manner or consists of a base threshold value and an adaptable dynamic value added to the base value or subtracted from the base threshold value depending on the behaviour of the first physical parameter. This dynamic value can, for example, be calculated as the average of measured results of the first physical parameter over a certain time interval. The base threshold value can also be used so that the threshold value is formed by the dynamic value.

The acceleration as first physical parameter or the measured values of the first physical parameter are converted in a step b) in the probe control unit 6 into a first state variable of the organism of the farm animal 2. In addition to the threshold-value-dependent operation of the probe device 1, the probe control unit 6 can also be operated selectively. Said unit is, for example, activated when a certain number of measured values (e.g. 32 measured values) of at least one of the sensor devices 51, 52 is present and a communication by interrupt is made to the probe control unit 6 which, for example, is executed as a microcontroller. Further grounds for activation of the probe control unit 6 can, for example be the reaching of defined measurement intervals (measurement, temperature, pH etc.) or predefined transmission intervals where an attempt at transmission of the measured data is started. Such intervals are implemented by means of a timer/counter (e.g. the clock generator 53 executed as RTC), here also the probe control unit 6 is activated by interrupt.

In other words, in one variant of the invention the probe control unit 6 is located as standard in a sleep mode and activation of the probe control unit 6 from the sleep mode and the subsequent conversion of the first physical parameter into a first state variable in the probe control unit 6 (see step b) further above) takes place depending on the presence of a minimum number of measured values and/or before reaching predefined measured values. A sleep mode is understood here as a complete deactivation or an energy-saving mode of the probe control unit 6.

Additionally or instead, the probe control unit 6 can also be located in a sleep mode with regard to the transmission of the first state variable to the evaluation unit 12 (step c) further above) until a certain predefined transmission interval is reached, i.e. a time at which a transmission of data takes place.

In the exemplary embodiment described, the motility, i.e. the ruminal or gastric activity is used as the first state variable of the organism of the farm animal 2. The motility substantially comprises intestinal movements of the gastro-intestinal tract 3 of the farm animal 2 which are manifest by corresponding contractions. In other words, motility designates within the disclosure of the present invention contractions of the gastro-intestinal tract 3 which act in the form of acceleration forces on the probe device 1. The motility as a first state variable is therefore expressed as acceleration forces which can be measured by the acceleration sensor of the probe device 1 as a result of movements of the gastro-intestinal tract 3 which propagate inter alia through the contents of the stomach. The motility can be used directly but also the duration of the contractions of the motility and/or their periodicity or frequency can be used as a first state variable.

The motility is therefore determined from the acceleration data inside the gastro-intestinal tract 3 of the cow 2. In this case, interfering signals such as, for example, the acceleration due to gravity can be filtered out from the acceleration data, for example, by direct component suppression. Without filtering out the acceleration due to gravity, for example position information can also be determined, i.e. standing and lying times of the farm animal.

By using a clock generator 53 or the RTC, the signal of the first state variable, here therefore the motility signal, is time-coded or matched with real time. Usually in this case the UTC ("universal coordinated time") is stored on the RTC. In one variant of the invention the RTC or the clock generator 53 is integrated in the probe control unit 6, this is therefore implemented as a microcontroller with integrated RTC. In a further variant time information can be transmitted from the evaluation unit 12 to the probe device 1 which combines this with its own relative time information (number of clock pulses or "ticks"). As has already been described further above, the clock generator 53 of the sensor unit 1 can also determine relative time values which are converted into absolute time values on the evaluation unit 12.

In addition, the signal of a temperature sensor 52 can be used to identify outliers of the signal of the first state variable which are obtained, for example, when the farm animal is drinking: if the motility is used as the first state variable, movements in the gastro-intestinal tract 3 which result from the medium ingested during drinking could be incorrectly interpreted as contractions. This can be prevented by taking into account the temperature signal. This temperature signal can also be taken into account in the evaluation unit 12. For this purpose, in addition to transmitting the first state variable, information on temperature, time and other status details can be transmitted to the evaluation unit 12.

In a step c) the first state variable or the values of the state variable is transmitted to the evaluation unit 12. In particular, here a wireless transmission by radio with a suitable protocol (e.g. LoRa™, ZigBee™, RFID, WLAN or others) is used, wherein preferably a suitable frequency range, e.g. 300 MHz to 450 MHz is used in which the permeability for radio waves in animals is particularly high.

This transmission can be accomplished continuously, in reality however a transmission is not always possible or desired because the cow 2 is not located in the receiving range of the evaluation unit 12 or because for energy-saving reasons the data should only be sent in packets. For this reason the storage element 7 designed as a RAM and/or ROM is provided. For example, the values of the first state variable can be stored during a measurement interval in the random access memory ("RAM") wherein they are then transferred from the temporary memory into an EEPROM, i.e. a read-only memory. The intermediate step with the EEPROM is in particular favourable in order to be able to store sufficient amounts of data before the next transmission to the evaluation unit 12 is possible.

According to the invention, the first state variable comprises a state variable which can be transmitted with a lower data transmission rate than the first physical parameter and/or a second state variable. This results in the advantage that the transmission of data to the evaluation unit 12 can take place with the lowest possible power consumption and the smallest possible bandwidth, which drastically increases the lifetime of the probe device 1 or its energy supply device 10.

In addition, the first state variable can be subjected to a compression process before transmission in order to further reduce the amount of data to be transmitted. Various methods are possible for this purpose, for example, median filtering for smoothing the signal, debouncing or a plausibility check (transmission of a first sequence or of an error code when the measured values do not lie within a known range).

In a step d) which is performed in the evaluation unit 12, a conversion of the first state variable into a second state variable takes place. In other words, the values of the second state variable are determined from the values of the first state variable. The second state variable comprises, for example, the rumination, the heart beat, the feeding and drinking times or the state and progress of the quantities relating to the digestive tract/process, for example, the duration of the contractions of the motility and/or their periodicity or frequency insofar as these have not already been determined on the probe unit 1 as the first state variable. In addition, further behaviour information in the form of activities such as standing, slow/fast movement and lying can be transmitted as the second state variable.

Rumination designates within the framework of the present disclosure the ruminating activity of the farm animal, in particular its intensity, duration and periodicity or frequency.

Through the choice of acceleration as a first physical parameter or motility and rumination as state variables, a lower power consumption on the probe device 1 can be achieved since the first physical parameter can be converted into the first state variable with lower computational expenditure than the first physical parameter into the second state variable and/or the first state variable into the second state variable. The computing-intensive, energy-consuming conversions therefore take place on the evaluation unit 12.

A first exemplary embodiment of the method according to the invention is described in detail with reference to the flow diagram in FIG. 5. Initially the probe device 1 is introduced into the gastro-intestinal tract 3 of a farm animal 2, in the depicted exemplary embodiment into the reticulum of a cow. For this purpose, the probe device 1 is implemented with a high density and adapted external dimension so that it remains in the reticulum after supply or after a short time initially in the rumen, comes into the reticulum and remains there.

20: By means of a tri-axial acceleration sensor for the three axes—x axis, y axis and z axis—of a Cartesian coordinate system, raw acceleration data inside the gastro-intestinal tract 3 of the cow 2 are determined as the first physical parameter. Acceleration values for the x y and z axis are therefore present.

The determination can be made, for example, with a sampling rate of 100 Hz, wherein the signal is resolved, for example, with 1 Bit=15 mg or better. In the present disclosure, the acceleration is given as a multiple or part of the average of the acceleration due to gravity which is designated by the letter "g" and when rounded is approximately 9.81 m/s$^{-2}$.

The measurement by the acceleration sensor is made either continuously or in an event-controlled manner wherein a threshold value—in particular for the acceleration—can be predefined for the activation or the beginning of measurement. This therefore comprises a beginning-of-measurement threshold value. The acceleration data are transmitted to the probe control unit 6 in which subsequently the measured values for the first physical parameter are converted into a motility signal as first state variable for the organism of the farm animal.

30: In a pre-processing, absolute values (hereinafter designated as "abs") of the acceleration of the three axes are formed. The absolute values are used since positive and negative acceleration values can occur on the individual axes. This step is optional—depending on which process is selected in the following steps, the forming of the absolute values can also be omitted.

40: The absolute values of the accelerations formed are summed. It holds that:

$$\text{Total acceleration} = \text{abs}(x\text{-axis}) + \text{abs}(y\text{-axis}) + \text{abs}(z\text{-axis}).$$

Figure 6:
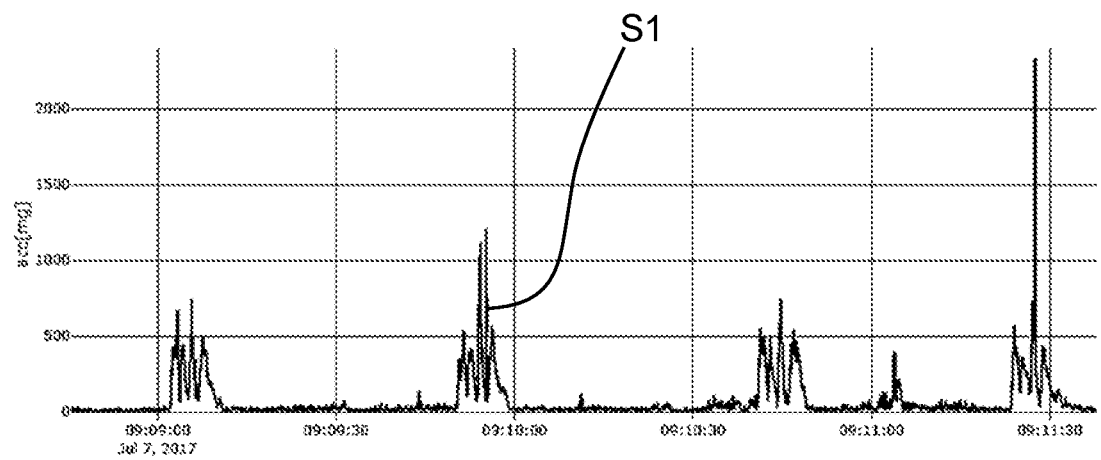
FIG. 6 shows measurement results of a first physical parameter from the process sequence in FIG. 5.

In the diagram of the measurement results in FIG. 6, the resulting sum signal S1 for the measured values of the first physical parameter is plotted versus a time axis. Here a time interval on 7 Jul. 2017 from 09:09 hours to 09:11 hours is selected as an example. On the y axis the acceleration "acc" is plotted in the units mg.

In this pre-processing phase an equidistant discrete signal is generated by using real-time information of a clock generator 53 or an RTC from the total values of the acceleration. The clock generator 53 can in this case, for example, output relative time information such as time or number of time units since the last transmission (accomplished after performing the sequences shown in FIG. 5 or in the previously described step c)) or since activating the probe unit 1. In other words, relative time information which is provided by a clock generator 53 can also be taken into account for carrying out the steps of the described method. This clock generator can be provided separately in the probe device 1 or as part of the probe control unit 6.

40*a*: Since the acceleration signal not only contains the motility but also other accelerations=movement of the farm animal, acceleration due to gravity, the influences due to ingesting feed described above—a filtering follows in order to improve the detectability of the motility. In this case, various filter methods can be used, for example, convolution filter (calculation of an average from the acceleration value of a data point and a certain number of its neighbouring data points, assignment of this average to this data points), "moving average" filter (for a window containing a specific number of data points an average is calculated, this window is displaced in an overlapping or iterative manner, i.e. the first data point from the observed window/section is deleted, the first data point after the window/section is added and a new average is calculated. For calculation of the average the data points occurring in the window can then be weighted arbitrarily) or discrete low-pass filters which allow values below a certain limiting threshold (here therefore of an acceleration value) to pass almost unattenuated. The acceleration due to gravity can, for example, be filtered out on the hardware side, i.e. directly at the triaxial acceleration sensor used here.

Figure 7:
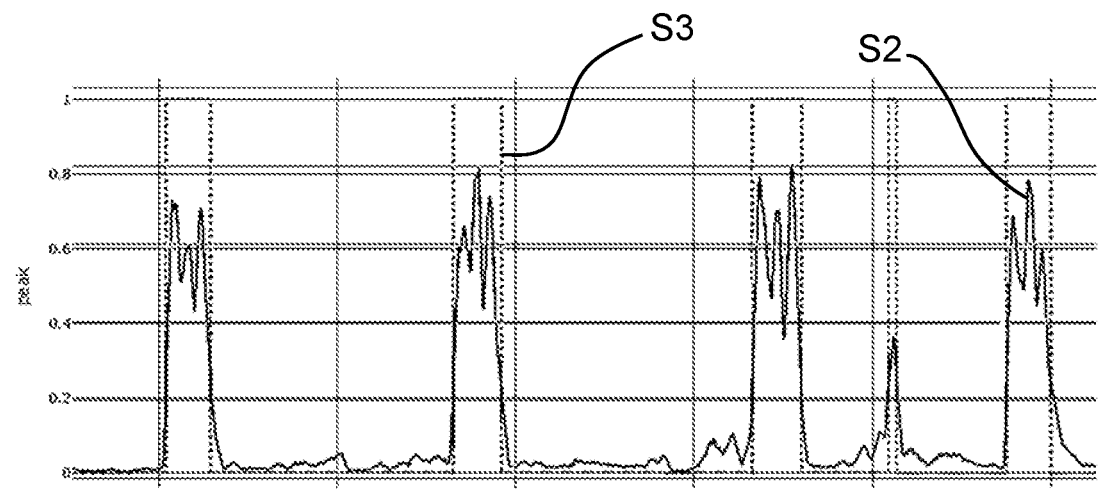
FIG. 7 shows results for a first state variable of the organism of a farm animal from the process sequence in FIG. 5.

In the depicted example, a discrete low-pass filter is used which therefore low-pass filters the total acceleration according to FIG. 4. FIG. 7 shows the low-pass filtered sum signal S2 of the sum signal S1 from FIG. 6.

In a variant not shown here the filtering can also be applied directly to the acceleration values of the x, y and z axis determined in step 20 before the total acceleration is formed.

50: A parameter threshold value is required to convert the measured values of the first physical parameter into a first state variable of the organism of the farm animal 2. In this case, either a fixed parameter threshold value can be used which is static and is adjustable via the configuring or configuration of the probe device 1 or via the transmitting device 8. In one variant an adaptive parameter threshold value can be used which consists of said fixed parameter threshold value which is supplemented by a dynamic threshold value which is dependent on the respective activity of the farm animal over a certain time interval. For this a moving average over a certain time interval can be determined from the low-pass-filtered sum signal according to 40 and 40*a*, which is shown in 50*a*. This dynamic threshold value can either be determined in the probe control unit 6 or in the evaluation unit 12 which then brings in the value via a suitable transmission path. In one variant, the fixed parameter threshold value=0 can also be set and the threshold value formed purely by the dynamic threshold value.

60: In a peak detection the measured values of the first physical parameter are converted into the first state variable.

In this case, the low-pass-filtered sum signal from 40 or 40*a* and the parameter threshold value from 50 or 50*a* serve as input quantities.

If a data point of the sum signal is greater than the parameter threshold value, the data point is assigned a binary "1", all the other data points are assigned a "0". Data points which are identical to the parameter threshold value can be assigned a "1" or a "0" depending on the configuring or configuration of the probe device 1.

The first state variable—in the present exemplary embodiment the motility—is thus obtained as a binary rectangular signal S3 whose behaviour is shown by the dashed line in FIG. 7. Data points with "1" correspond to a contraction of the gastro-intestinal tract 3, at "0" there are no gastric movements. In particular, the contraction of the reticulum ("reticulum" or also called reticulum) is determined when the probe device 1 is disposed there, the contractions of the other regions of the gastro-intestinal tract 3 (in particular dorsal rumen sac, atrium, ventral rumen sac) are not measured.

In the peak detection the low-pass-filtered sum signal of the absolute acceleration values is thus converted into a binary rectangular signal which corresponds to the motility as the first state variable of the organism of the farm animal. This rectangular signal as a sequence of "0" and "1" can be transmitted with a lower data transmission rate than the sum signal of the accelerations. As a result, the power consumption during transmission of the measured values of the first state variable to the evaluation unit 12 can be reduced significantly. In a variant of the invention which is not discussed further here, however, the duration of the contractions of the motility and/or their periodicity can also be used as the first state variable by means of corresponding evaluation of the rectangular signal.

70: In order to further reduce the amount of data to be transmitted, the rectangular signal is "downsampled" or downsampled in a post-processing. At the described sampling rate of the acceleration sensor of 100 Hz, a rectangular signal also with 100 Hz is obtained after the peak detection 60.

In the post-processing a downsampling is applied to this, e.g. by a factor of 50 so that only a 2 Hz rectangular signal must be transmitted to the evaluation unit 12. In this case, with the assumed clocking factor of 50, in each case 50 data points of the rectangular signal are collected from the peak detection 60—if more than half these data points are "1"— "1" is assumed as total output, for "0" accordingly "0". The dominant binary value of the selected quantity of data points thus determines its total value.

In exemplary embodiments, the said post-processing or downsampling can also take place at an earlier time point of the described method, for example, after determining the measured values in step 20 or after filtering in step 40*a*.

A further reduction in the amount of data to be transmitted can be achieved by compressing the amount of data e.g. by run-length encoding ("run-length encoding" or "RLE"; only those positions at which the binary value changes are marked) or transmitting information only to those regions of the rectangular signal in which the binary value is "1".

Figure 5:
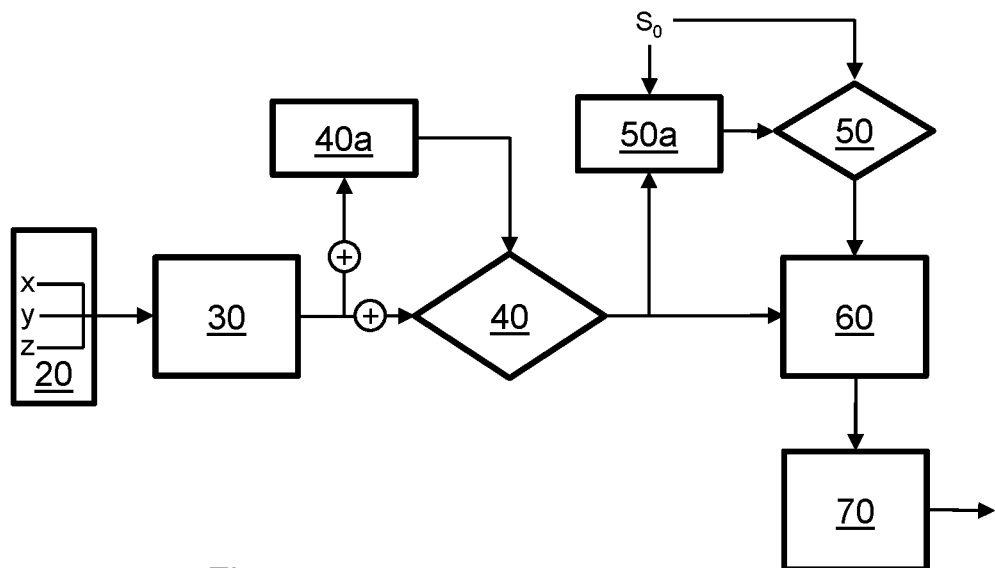
FIG. 5 shows a flow diagram of a first variant of the method according to the invention.

The arrow pointing from the block 70 in FIG. 5 indicates that the result of the peak detection 60 or the post-processing 70 is transmitted to the evaluation unit 12 wherein in the meantime storage in a storage element 7 of the probe device 1 can take place in order to transmit the measured values of the first state variable in a bundled manner.

The resulting binary values are therefore firstly stored in a cache on RAM, after a measurement interval has elapsed, the temporary cache is transferred to an EEPROM as read-only memory. This step is necessary in order to ensure a sufficiently large storage capacity for the measured values of the first state variable before the next transmission to the evaluation unit 12 takes place. Otherwise, data gaps can occur in the measured values of the first state variable.

After transmitting the binary rectangular signal of the first state variable to the evaluation unit 12, the first state variable is converted into the second state variable on the evaluation unit.

Starting from the motility as the first state variable, the second state variable can comprise the pulse width and therefore the durations of the contractions and/or their periodicity—that the time which passes between two successive contraction phases—and/or their frequency and therefore the rumination or ruminating times.

The conversion of the motility as the first state variable into the rumination as the second state variable is accomplished, for example, by identifying regions of the binary rectangular signal in which the pulse width of the motility initially increases and then remains constant until it changes again. Such a region is identified as ruminating activity. This identification is preferably made by using suitable algorithms, for example, machine learning algorithms. The computational expenditure for such algorithms is comparatively high, therefore it is favourable to perform the determination of the second state variable from the first state variable in the evaluation unit 12 whereas the relatively resource-saving conversion of the first physical parameter into the first state variable is performed in the probe control unit 6.

This in particular also results in the advantage that the algorithm used for the conversion of the first into the second state variable can be amended or adapted without great expense—if the conversion were to take place in the probe device 1, the amendment to the algorithms would need to be made via updates which bring about a restriction of the transmission capacity available for the probe devices 1 which is disadvantageous for the use of the probe devices 1 as intended in production operation.

Figure 8:
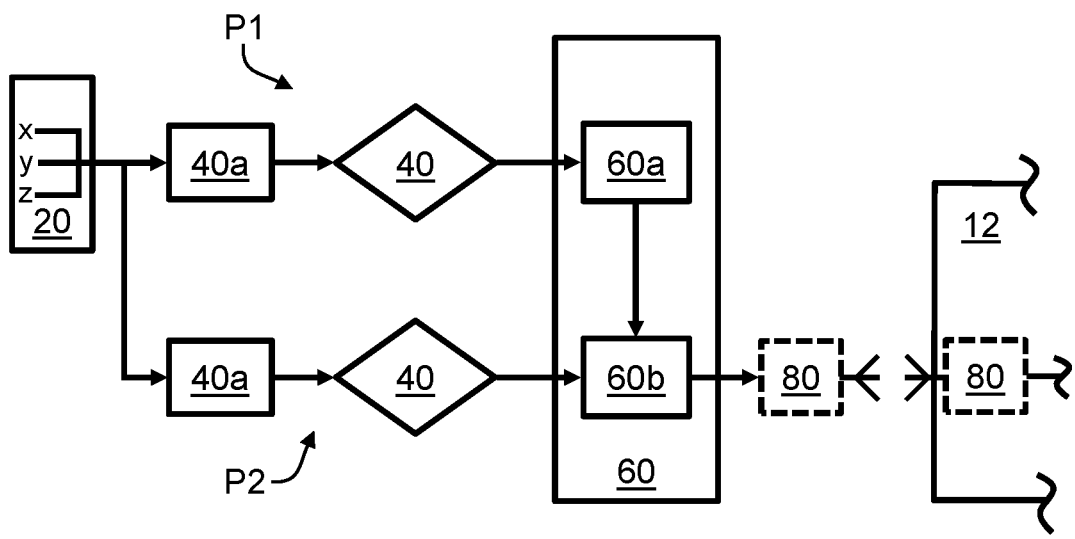
FIG. 8 shows a flow diagram of a second variant of the method according to the invention.

FIG. 8 shows a second exemplary embodiment of the method according to the invention at its beginning as well as in the first exemplary embodiment according to FIG. 5 the introduction of a probe device 1 into the gastro-intestinal tract 3 of a farm animal 2.

20: Again acceleration values are determined for an x, y and z axis of a Cartesian coordinate system by means of an acceleration sensor.

The following steps are carried out in two parallel paths. The step 30 shown in FIG. 5 is not shown in FIG. 8 since it is optional and need not necessarily be carried out. When determining the motility as the first state variable, in the upper path P1 in FIG. 8 from the acceleration values, an identification of the position of a motility contraction is carried out, i.e. the time at which the contraction takes place; in the lower path P2 in FIG. 8 a contraction width is determined, i.e. the duration of the contraction, in particular using the results of the upper path P1.

40a: In this filter step an axially selective filtering takes place for both paths P1, P2 as described in the first exemplary embodiment. "Axially selective" means here that the acceleration values of the x, y and z axis are filtered separately, e.g. by using a bandpass filter. As a result, noise and interference can be removed particularly effectively, e.g. movement activities of the farm animal which could disadvantageously influence subsequent sequences of the method according to the invention.

40: The filtered signals of the x, y and z axis are combined in an aggregation step to form a sum signal which is used for the following steps. In this case, various sequences are possible. The following procedure has already been described in connection with FIG. 5:

$$\text{Total acceleration} = \text{abs}(x\text{-axis}) + \text{abs}(y\text{-axis}) + \text{abs}(z\text{-axis}).$$

However, the following variants can also be used:

$$\text{Total acceleration} = x\text{-axis}^2 + y\text{-axis}^2 + z\text{-axis}^2; \text{ or}$$

$$\text{Total acceleration} = \text{sqrt}(x\text{-axis}^2 + y\text{-axis}^2 + z\text{-axis}^2).$$

The abbreviation "sqrt" here stands for "square root", i.e. the root; the symbol "^2" designates the square function in the usual manner. These variants can be used on both paths P1, P2. In particular on the lower path P2 variants can additionally be used to determine the contraction width such as, for example:

$$\text{Total acceleration} = \arctan(y\text{-axis}, z\text{-axis}),$$

wherein here y-axis and z-axis are selected since the position of the acceleration sensor in the probe unit 1 and the fact that the probe unit 1 is substantially cylindrical should be taken into account Using $r = \text{sqrt}(x\text{-axis}^2 + y\text{-axis}^2 + z\text{-axis}^2)$ the following solution can also be used:

$$\text{Total acceleration} = \arctan(r, x\text{-axis}).$$

Fundamentally it should be said that the sequence of filter step and aggregation step can also be selected differently so that the aggregation can take place before the filtering or a first filter step takes place before the aggregation and a second follows the aggregation. In particular, the two paths P1, P2 can also be executed differently with regard to the number and sequence of these steps. The positioning of the blocks 40a and 40 in FIG. 8 is only one of several possibilities.

60: In the depicted exemplary embodiment according to FIG. 8 the conversion of the measured values of the first physical parameter takes place differently from the execution in FIG. 5. Here the paths P1, P2 are combined again.

60a: In the upper path P1 in order to determine the position, the time positions of the motility contractions are determined by application of a peak detection algorithm. In this case, the following parameters which are either stored in the probe unit 1, determined dynamically or incorporated via the evaluation unit 12 as used as input:

threshold value, in particular adaptive threshold value which similarly to the parameter threshold value from FIG. 5 which is determined as in steps 50, 50a depicted there (for reasons of clarity these steps are not shown in FIG. 8) by means of a moving average or "rolling root mean square";

minimal contraction distance, designates the shortest permissible time interval between two contractions of the reticulum;

total acceleration; the filtered and aggregated raw signal of the acceleration sensor as described above.

The time positions of the contractions are now determined so that all the values of the total acceleration which are greater than the threshold value are assigned the value "1", the value "0" applies for the remaining values. The values of the total acceleration to which the value "1" is assigned are hereinafter designated as "peaks".

Figure 9:
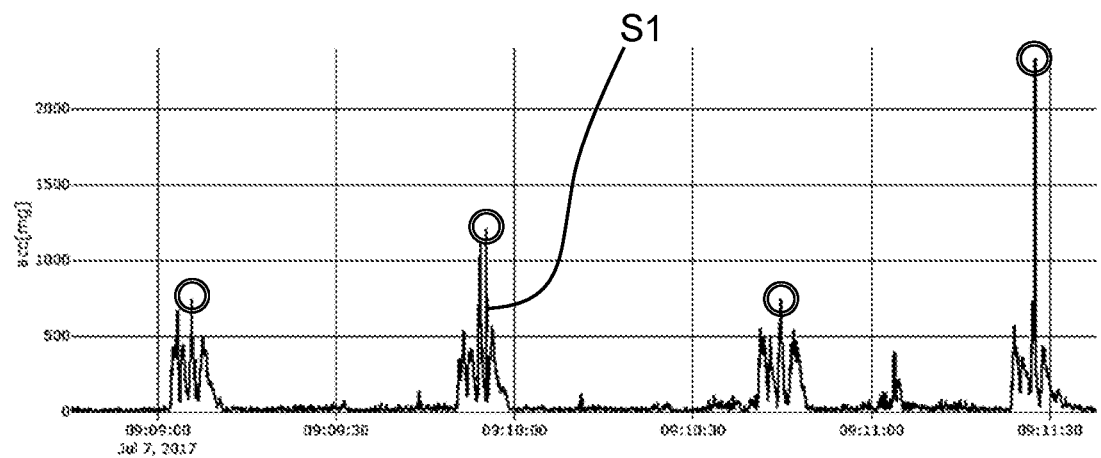
FIG. 9 shows measurement results of a first physical parameter from the process sequence in FIG. 8.

The "peaks" are now further selected as to whether they lie closer to one another than the above-defined minimal contraction distance. In the case of "peaks" whose distance from one another lies below the minimum contraction distance, that "peak" whose total acceleration is lower is eliminated. The larger "peak" is retained. "Peaks" are eliminated until the time interval between the remaining "peaks" is greater than the defined minimal contraction distance. FIG. 9 now shows an application of this method to the sum signal S1 from FIG. 6, wherein the identified and remaining "peaks" are characterized by circles with a double line.

Figure 10:
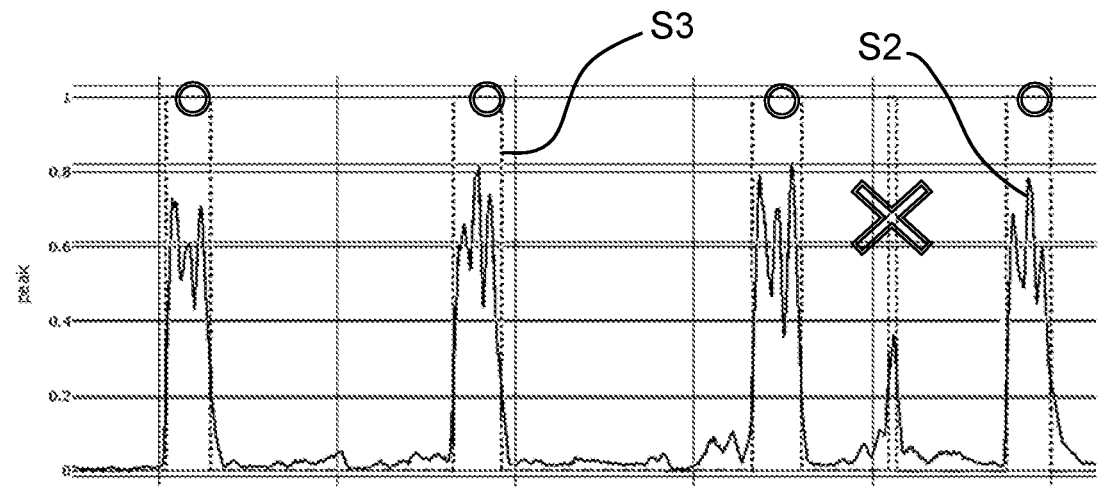
FIG. 10 shows result for a first state variable of the organism of a farm animal from the process sequence in FIG. 8.

60*b*: In the lower path P2 in order to determine the duration or width of the contractions, a parameter which defines a minimal distance between "peaks" (minimal peak distance) is applied to the total acceleration in addition to a threshold value for the identification of "peaks". By this means "peaks" which are closer to one another than the minimal peak distance are combined to a common "peak". As can be seen in FIG. 10, this results in a sequence of regions with the value "0"—no "peak"—and of regions with the value "1"—combined "peaks" which before application of the parameter lay closer to one another than the defined minimal peak distance. Now the result of 60*a* in the upper path P1 is applied to this: those combined "peaks" which were not identified as position of a contraction in step 60*a* are eliminated—one "peak" in FIG. 10 is therefore deleted.

As a result of step 60 with substeps 60*a* and 60*b* in FIG. 8 a rectangular signal is therefore again obtained which again combines paths P1, P2.

In the method according to FIG. 8, a post-processing can also be used as was described in connection with FIG. 5. However, it can be performed at one or more different places and is therefore not indicated for reasons of clarity.

The second exemplary embodiment shown in FIG. 8 has the advantage that the motility signal can be determined more precisely which facilitates the further method—in particular the determination of the second state variable, e.g. the periodicity, i.e. the time between contractions. In addition, signals which should not be considered as motility signals can be eliminated.

Following the conversion of the measured values of the first physical parameter into the first state variable, a validation step 80 can also be carried out. The validation step 80 can either be performed on the probe unit 1 before transmission to the evaluation unit 12, i.e. as a substep of step b) or before carrying out step c) of the method according to the invention or only on the evaluation unit 12 as part of step d) of the method according to the invention. For this reason the validation step 80 is shown in FIG. 8 as dashed boxes both adjoining step 60 and also as pertaining to the evaluation unit 12. Fundamentally it would also be possible that such a validation takes place twice, i.e. that both dashed steps 80 are executed.

A validation step 80 is in particular necessary because as a result of the complex environment of the data taking—movement of the farm animal, influence of environmental conditions, unexpected results—incorrect measurement data cannot be excluded. When determining the motility from acceleration values, incorrect measurements can occur as a result of high movement activity of the farm animal or if the probe unit 1 moves out of the reticulum.

In the depicted exemplary embodiment, the validation step 80 can be performed, for example so that the first state variable in the form of the motility signal is validated. In this motility validation it is checked whether the pulse widths—substantially therefore the duration of the contractions for which the value of the rectangular signal is "1"—and/or the threshold values applied in step 60 which are partially adaptively varied, are plausible. If it is known that the pulse width must lie between 5 and 15 seconds, a determined pulse width of more than 30 seconds can be identified as incorrect.

Depending on which value is used as the first state variable in the validation step 80 it can be checked whether a resulting periodicity is plausible and/or acting accelerations during the contraction are plausible. Corresponding plausibility values are stored on the probe unit 1 and/or the evaluation unit 12 or are exchanged between these, in particular to the effect that corresponding values are transmitted from the evaluation unit 12 to the probe unit 1.

Favourably this validation step 80 is carried out on the probe unit 1 because it can thereby be prevented that incorrect data is transmitted at the expense of energy and bandwidth. Data which do not pass the validation step 80 are only transmitted as error signals. Such data are then not taken into account on the evaluation unit 12.

Naturally the validation step 80 can also take place on the evaluation unit 12 wherein then only plausible data is further processed.

In the computer-assisted methods described in the exemplary embodiments to determine at least one state variable of the organism of at least one farm animal 2, a first physical parameter is therefore determined on a probe device 1, for example, acceleration values with the aid of a triaxial acceleration sensor and in a probe control unit 6 converted into the motility as first state variable of the organism of a farm animal 2 in the form of a binary rectangular signal from which information relating to the organism of the farm animal can be determined as previously. This process requires only low computational capacities and brings about a reduction in the amount of data. In addition, the risk of errors in the source code is reduced by the comparatively simple programming.

This first state variable is transmitted to an evaluation unit 12 by means of a suitable transmission method, in particular a wireless method. The amount of data to be transmitted is comparatively small which reduces the transmission time, the associated power consumption on the probe device 1 and the required bandwidth. In the evaluation unit 12 the first state variable is converted in comparatively more expensive processes into a second state variable, the rumination or ruminating activity. This conversion can be interpreted in a resource-intensive manner without any problems because the evaluation unit 12—usually a computer or server—has sufficient computational capacity and can be easily supplied with energy as a stationary unit.

A long-term correct use of the probe device 1 with the best possible exchange of information with the evaluation unit 12 can thus be ensured.

The invention claimed is:

1. A method for determining at least one state variable of an organism of at least one farm animal, wherein at least one probe device for measurement of at least one physical parameter is disposed in a gastro-intestinal tract of the farm animal and at least one evaluation unit is disposed outside the gastro-intestinal tract of the farm animal, characterized by the following steps:

a1) using the at least one probe device to determine an acceleration of the at least one probe device in all three spatial directions of a Cartesian coordinate system, wherein the determination takes place in at least one of the following manners: continuously: at regular intervals: continuously as soon as the at least one physical parameter measured by the at least one probe device has exceeded a threshold value: at regular intervals, as soon as the at least one physical parameter measured by the at least one probe device has exceeded the threshold value; continuously or at regular intervals for a predefined time interval as soon as the at least one physical parameter measured by the at least one probe device exceeds the threshold value as a first of the at least one physical parameter of the at least one probe device;

a2) determining the acceleration of step a1) as the at least one first physical parameter by carrying out at least one of the following steps: summing absolute values of the acceleration values determined in step a1), summing squares of the acceleration values determined in step a1), root of the sum of the squares of the acceleration values determined in step a1) arctan of the acceleration values determined in step a1) for a y axis and a z axis of the Cartesian coordinate system, arctan of the root of the sum of the squares of the acceleration values determined in step a1) and an x axis of the Cartesian coordinate system;

b) converting the at least one first physical parameter into a motility value as a first state variable of the organism of the farm animal in a probe control unit of the at least one probe device, wherein values of the at least one first physical parameter that are greater than or equal to a threshold value, are assigned a value of a binary "1" and measured values of the at least one first physical parameter that are lower than the threshold value are assigned a value "0", with the threshold value either being stored predefined on the at least one probe device or being transmitted from the at least one evaluation unit in an occasion-related manner to the at least one probe device or consisting of a base threshold value and an adaptable dynamic value added to the base threshold value or subtracted from the base threshold value depending on the behaviour of the at least one first physical parameter;

c) wirelessly electronically transmitting the first state variable as a binary rectangular signal by the at least one probe device to the at least one evaluation unit; and d) converting the first state variable into a second state variable in the at least one evaluation unit.

2. The method according to claim 1, characterized in that the first state variable comprises a state variable which in step c) is transmitted with a lower data transmission rate than the at least one first physical parameter.

3. The method according to claim 1, characterized in that the at least one first physical parameter is converted into the first state variable with lower computational expenditure than the at least one first physical parameter into the second state variable and/or the first state variable into the second state variable.

4. The method according to claim 1, characterized in that the first state variable in step b) comprises a duration and/or a periodicity and/or a frequency of a motility.

5. The method according to claim 1, characterized in that in step b) the first state variable is verified with a real-time signal of a clock generator provided in the at least one probe device and/or a temperature signal of a temperature sensor provided in the at least one probe device.

6. The method according to claim 1, characterized in that the second state variable in step d) comprises one of the following state variables of the organism of the farm animal: rumination, heart beat, feeding time.

7. The method according to claim 1, characterized in that directly before step c) in the probe control unit of the at least one probe device and/or before carrying out step d) in the at least one evaluation unit a validation step is carried out in order to check a plausibility of the values of the first state variable of the organism of the farm animal.

8. A probe device for measuring at least one state variable of the organism of the farm animal, wherein the probe device is arranged in the gastro-intestinal tract of the farm animal and comprises at least the following components arranged in a housing:

at least one sensor element for measuring the at least one physical parameter in the gastro-intestinal tract of the farm animal, at least one transmitting device having at least one antenna for the wireless transmission and receipt of information and the probe control unit which is adapted for carrying out steps a1) to c) of the method according to claim 1.

9. The probe device according to claim 8, characterized in that at least one of the following sensor elements is provided: an acceleration sensor for measuring an acceleration in all three spatial directions of the Cartesian coordinate system, a temperature sensor, a pH sensor, a clock generator, a real-time clock, and a camera element.

10. The probe device according to claim 8, characterized in that at least one storage element connected to the probe control unit is provided, wherein the probe control unit comprises at least one RAM and/or at least one ROM storage element.

11. A system comprising at least one evaluation unit and at least one probe device according to claim 8, wherein the method according to claim 1 is carried out with the system.

* * * * *

UNITED STATES PATENT AND TRADEMARK OFFICE
CERTIFICATE OF CORRECTION

PATENT NO. : 12,064,230 B2
APPLICATION NO. : 17/292949
DATED : August 20, 2024
INVENTOR(S) : Michael Astl et al.

Page 1 of 1

It is certified that error appears in the above-identified patent and that said Letters Patent is hereby corrected as shown below:

In the Claims

In Column 16, Line 60, change "continuously: at" to "continuously; at".
In Column 16, Line 61, change "intervals: continuously" to "intervals; continuously".
In Column 16, Line 63, change "value: at" to "value; at".
In Column 17, Line 10, change "a1), root" to "a1), taking the root".
In Column 17, Line 11, change "in step a1)" to "in step a1),".
In Column 17, Line 12, change "arctan of" to "taking the arctan of".
In Column 17, Line 14, change "system, arctan" to "system, taking the arctan".
In Column 17, Line 23, change "value, are" to "value are".
In Column 17, Line 24, change ""1" and measured" to ""1", and measured".

Signed and Sealed this
Twenty-fifth Day of February, 2025

Coke Morgan Stewart
*Acting Director of the United States Patent and Trademark Office*